United States Patent [19]

Kmiec

[11] Patent Number: 5,756,325
[45] Date of Patent: *May 26, 1998

[54] COMPOUNDS AND METHODS FOR SITE DIRECTED MUTATIONS IN EUKARYOTIC CELLS

[75] Inventor: Eric B. Kmiec, Malvern, Pa.

[73] Assignee: Thomas Jefferson University, Philadelphia, Pa.

[*] Notice: The term of this patent shall not extend beyond the expiration date of Pat. No. 5,565,350.

[21] Appl. No.: 709,982

[22] Filed: Sep. 9, 1996

Related U.S. Application Data

[63] Continuation of Ser. No. 353,657, Dec. 9, 1994, Pat. No. 5,565,350, which is a continuation-in-part of Ser. No. 164, 303, Dec. 9, 1993, abandoned.

[51] Int. Cl.$^6$ .......................... C12N 15/11; C12N 15/63; C07H 21/00
[52] U.S. Cl. .................... 435/172.3; 435/320.1; 536/23.1; 536/25.3
[58] Field of Search ................. 435/172.3, 240.2, 435/252.3, 254.11, 320.1; 536/23.1, 25.3

[56] References Cited

U.S. PATENT DOCUMENTS

| | | | |
|---|---|---|---|
| 4,503,151 | 3/1985 | Paddock | 435/6 |
| 4,873,191 | 10/1989 | Wagner et al. | 435/172.3 |
| 4,882,279 | 11/1989 | Cregg | 435/172.3 |
| 4,950,599 | 8/1990 | Bertling et al. | 435/172.3 |
| 5,013,830 | 5/1991 | Ohtsuka et al. | 536/25.1 |
| 5,589,369 | 12/1996 | Seidman et al. | 435/172.3 |

FOREIGN PATENT DOCUMENTS

| | | |
|---|---|---|
| WO 93/22443 | 11/1993 | WIPO. |
| WO 94/04032 | 3/1994 | WIPO. |
| WO 94/23028 | 10/1994 | WIPO. |

OTHER PUBLICATIONS

Hug et al. Liposomes for the transformation of eukaryotic cells. Biochimica et aBiophysica Acts vol. 1097, pp. 1–17, 1991.

Potter et al. Enhancer–dependent expression of human kappa immunoglobulin genes intorduced into mouse pre–B lymphocytes by electroporation. Proc. Natl. Acad. Sci. USA vol. 81, pp. 7161–7165, 1984.

Roberts, R.W., & Crothers, D.M., "Stability and Properties of Double and Triple Helices: Dramatic Effects of RNA or DNA Backbone Composition", Science 258:5087,1463–1466 (1992).

Shimizu et al., "Oligo(2'–O–methyl)ribonucleotides—Effective probes for duplex DNA", FEBS Letters 302:2, 155–158 (1992).

Monia et al., "Selective Inhibition of Mutant Ha–ras mRNA Expression by Antisense Oligonucleotides", J. Biol Chem 267:28, 19954–19962 (1992).

Monia et al., "Evaluation of 2'–Modified Oligonucleotides Containing 2'–Deoxy Gaps as Antisense Inhibitors of Gene Expression", J Biol Chem 268:19, 14514–14522 (1993).

Lesnik et al., "Oligodeoxynucleotides Containing 2'–O–Modified Adenosine: Synthesis and Effect on Stability of DNA:RNA Duplexes", Biochemistry 32:7832–7838 (1993).

Shimizu et al., "Effects of 5–Methyl Substitution in 2'–O–Methyloligo–(Pyrimidine)Nucleotides on Triple–Helix Formation", Bio & Med Chem Ltrs 4:8, 1029–1032 (1994).

Taparowski et al., "Activation of the T24 Bladder Carcinoma Transforming Gene is Linked to a Single Amino Acid Change", Nature 300:762 (1982).

Sukamar et al., "Induction of Mammary Carcinomas in Rats by Nitroso–Methylurea Involves Malignant Activation of H–ras–1 Locus by Single Point Mutations", Nature 306:658 (1983).

Caruthers, "Gene Synthesis Machines: DNA Chemistry and Its Uses", Science 230:281–285 (1985).

Thomas and Capecchi, "Site–Directed Mutagenesis by Gene Targeting in Mouse Embryo–Derived Stem Cells", Cell 52:503 (1987).

Moerschell et al., "Transformation of Yeast with Synthetic Oligonucleotides", PNAS USA 85:524–528 (1988).

Brinster et al., "Targeted Correction of a Major Histocompatibility Class II $E_\alpha$ Gene by DNA Microinjected into Mouse Eggs", PNAS USA 86:7087 (1989).

Capecchi, "Altering the Genome by Homologous Recombination", Science 244:1288 (1989).

Perreault et al., "Mixed Deoxyribooligonucleotides with Catalytic Activity", Nature 344:565 (1990).

Scaringe et al., "Chemical Synthesis of Biologically Active Oligonucleotides Using β–Cyanoethyl Protected Ribonucleoside Phosphoraidites", Nuc Acids Res 18:5433–5441 (1990).

Wahls et al., "The Z–DNA Motif d(TG)$_{30}$ Promotes Reception of Information during Gene Conversion Events while Stimulating Homologous Recombination in Human Cells in Culture", Mol Cell Biol 10:785–793 (1990).

Yang et al., "Mixed DNA/RNA Polymers Are Cleaved by the Hammerhead Ribozyme", Biochemistry 29:11156–11160 (1990).

Chou, "High–Resolution NMR Studies of Chimeric DNA–RNA–DNA Duplexes, Heteronomous Base Pairing, and Continuous Base Stacking at Junctions", Biochemistry 30:5248–5257 (1991).

(List continued on next page.)

Primary Examiner—James Ketter
Assistant Examiner—John S. Brusca
Attorney, Agent, or Firm—Joan E. Switzer; Daniel Hansburg; Thomas E. Friebel

[57] ABSTRACT

The present invention concerns a polynucleotide having both ribonucleotides and deoxyribonucleotides in a first strand and solely deoxyribonucleotides in a second strand; wherein the strands are Watson-Crick paired and are linked by an oligonucleotide so that the polynucleotide has at most a single 3' and a single 5' end. These ends can be ligated so that the polynucleotide is a single continuous circular polymer. The polynucleotide can be used to induce specific alterations in targeted genes.

62 Claims, 1 Drawing Sheet

OTHER PUBLICATIONS

Valencius and Smithies, "Double–Strand Gap Repair in a Mammalian Gene Targeting Reaction", Mol Cell Biol 11:4389 (1991).

Hendry et al., "A Ribozyme with DNA in the Hybridising Arms Displays Enhanced Cleavage Ability", Nuc Acids Res 20:5737–5741 (1992).

Taylor et al., "Chimeric DNA–RNA Hammerhead Ribozymes Have Enhanced in vitro Catalytic Efficiency and Increased Stability in vivo", Nuc Acids Res 20:4559–4565 (1992).

Usman et al., "Large Scale Chemical Synthesis, Purification and Cystallization of RNA–DNA Chimeras", Nuc Acids Res 20:6695–6699 (1992).

Usman and Cedergen, "Exploiting the Chemical Synthesis of RNA", Trends Bioch Sci 17:334–339 (1992).

Yamamoto et al., "Parameters Affecting the Frequencies of Transformation and Co–Transformation with Synthetic Oligonucleotides in Yeast", Yeast 8:935–948 (1992).

Egli et al., "Conformational Influence of the Ribose 2'–Hydroxyl Group: Crystal Structures of DNA–RNA Chimeric Duplexes", Biochemistry 32:3221–3227 (1993).

Sawata et al., "Enhancement of the Cleavage Rates of DNA–Armed Hammerhead Ribozymes by Various Divalent Metal Ions", Nuc Acids Res 21:5656–5660 (1993).

Shimayama, "Nuclease–Resistant Chimeric Ribozomes Containing Deoxyribonucleotides and Phosphorothioate Linkages", Nuc Acids Res 20:4559–4565 (1992).

Ban et al., "A Single 2'–Hydroxyl Group Converts B–DNA to A–DNA", J Mol Biol 236:275–285 (1994).

Salazar et al., "The Solution Structure of the r(gcg)d-(TATACCC):d(GGGTATACGC) Ozaki Fragment Contains Two Distinct Duplex Morphologies Connected by a Junction", J Mol Biol 241:440–455 (1994).

Swiderski et al., "Polystyrene Reverse–Phase Ion–Pair Chromatography of Chimeric Ribozomes", Annal Biochem 216:83–88 (1994).

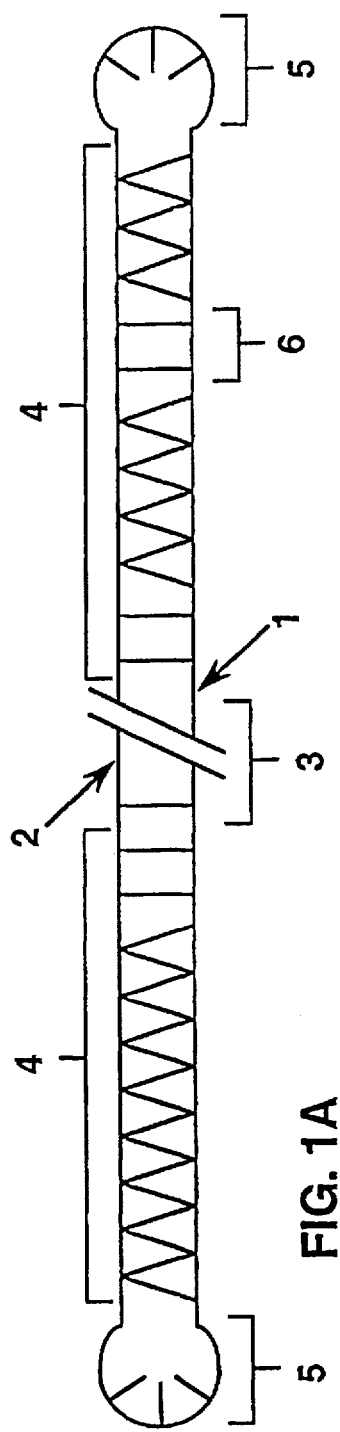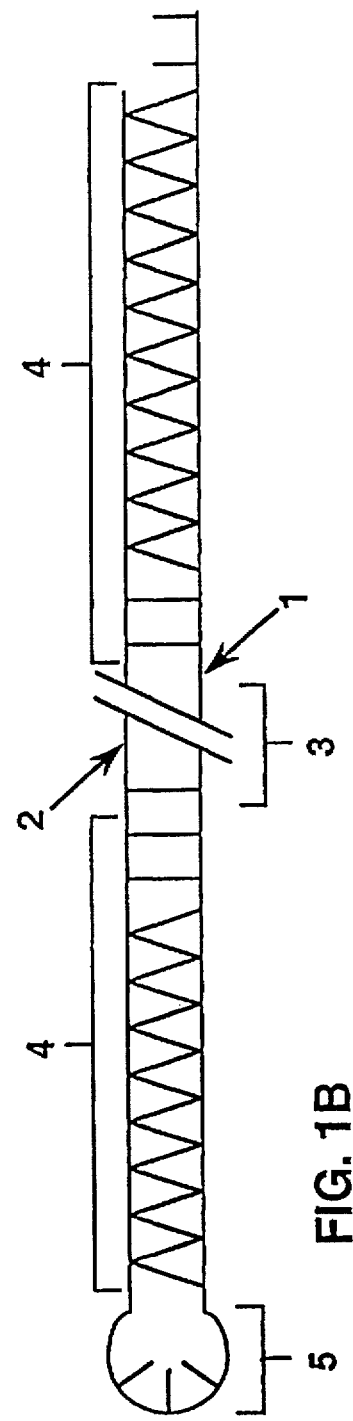

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA/RNA ( i x ) FEATURE:
        ( A ) NAME/KEY: -
        ( B ) LOCATION: 19..32
        ( D ) OTHER INFORMATION: /label=a
            / note= "RNA"

( x i ) SEQUENCE DESCRIPTION: SEQ ID NO:1:

TGCCGATCGG CAACTTTTGU UGCCGAUCGG CAAATTT                        37

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TGCCGATCGG CAACTTTTGT TGCCGATCGG CAAATTT                        37

( 2 ) INFORMATION FOR SEQ ID NO:3:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA/RNA ( i x ) FEATURE:
        ( A ) NAME/KEY: -
        ( B ) LOCATION: 2..5
        ( D ) OTHER INFORMATION: /label=b -continued

```
           / note= "RNA"

( i x ) FEATURE:
        ( A ) NAME/KEY: -
        ( B ) LOCATION: 10..21
        ( D ) OTHER INFORMATION: /label=d
           / note= "RNA"

( i x ) FEATURE:
        ( A ) NAME/KEY: -
        ( B ) LOCATION: 51..52
        ( D ) OTHER INFORMATION: /label=f
           / note= "RNA"

( x i ) SEQUENCE DESCRIPTION: SEQ ID NO:3:

CACACCGACG GCGCCCACCA CTTTGTGGTG GGCGCCGTCG GTGTGGGTTT GCC        53

( 2 ) INFORMATION FOR SEQ ID NO:4:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:4:

GCCCACACCG ACGGCGCCAC CAC        23
```

COMPOUNDS AND METHODS FOR SITE DIRECTED MUTATIONS IN EUKARYOTIC CELLS

This is a continuation of application Ser. No. 08/353,657, filed Dec. 9, 1994, now U.S. Pat. No. 5,565,350 which is a Continuation-in-Part of patent application Ser. No. 08/164,303 now abandoned, filed Dec. 9, 1993, which is hereby incorporated by reference in its entirety.

FIELD OF THE INVENTION

The present invention concerns the field of molecular genetics. Particularly it concerns nucleic acid compounds and methods of their use to introduce specific genetic alterations into living cultured eukaryotic cells. More particularly it concerns substantially Watson-Crick paired, duplex nucleic acids wherein a portion of one strand of the duplex comprises a 2'-O or 2'-OMe ribose containing nucleotides and the remainder comprise deoxyribose nucleotides.

BACKGROUND TO THE INVENTION
CHIMERIC AND/OR HYBRID DUPLEX NUCLEIC ACIDS

The field of the invention concerns nucleic acids. Nucleic acids are heteropolymers, i.e., polymers of non-identical subunits, which are linked by oriented phosphodiester bonds or their derivatives, into polymers.

Duplex nucleic acids are nucleic acids wherein each base of a first strand of the duplex corresponds to a base of a second strand of the duplex according to the scheme in which uracil or thymine and adenine correspond and cytosine and guanine correspond. Anti-parallel duplex strands having these correspondences are said to be Watson-Crick paired. Duplex nucleic acids can be of two major types, ribonucleic acids and deoxyribonucleic acids. Each ribonucleotide has an equivalent deoxyribonucleotide, e.g., adenosine and deoxyadenosine, cytidine and deoxycytidine, guanosine and deoxyguanosine, uridine and thymidine. As used in the field, a nucleic acid in which both ribonucleotides and deoxyribonucleotides are present in the same strand is termed a mixed or chimeric (hereinafter "chimeric") nucleic acid. A duplex nucleic acid in which deoxyribonucleotides and ribonucleotides correspond with each other is termed a hybrid-duplex. When two strands form a region of duplex nucleic acid for less than all of their bases, the resultant molecule is termed a heteroduplex.

Most often, the two strands of a duplex nucleic acid are not covalently bonded but are associated only by Watson-Crick pairing. However, the two strands of a duplex can be linked by an oligonucleotide to form a single polymer. The linking oligonucleotide is not Watson-Crick paired. The heteroduplex in which the first and second strands are portions of a single polymer is termed a "hairpin duplex" or a "stem and loop" structure. The former term will be used hereinafter.

As used herein chimerism is a property of a nucleic acid polymer and hybridism is a property of a duplex. For example, an mRNA and its template form a hybrid duplex though neither is chimeric, while, for example, the chimeric octanucleotides 5'd(TTTT)-r(CCCC)3' and 5'r(GGGG)-d(AAAA)3' will form a Watson-Crick duplex with each other but the resultant duplex is not a hybrid-duplex. A duplex nucleic acid which is not a hybrid-duplex is termed hereinafter a "homo-duplex". Unless specifically noted otherwise, a homo-duplex nucleic acid refers only to a deoxynucleotide containing duplex. Lastly, note that while those in the field refer to the formation of a Watson-Crick duplex as "hybridization," even where there is no hybrid-duplex nucleic acids.

Those interested in the study the structure of chimeric and/or hybrid duplex nucleic acids by X-ray diffraction and 2-dimensional NMR have synthesized chimeric nucleic acids and hybrid duplex nucleic acids for use in their studies. See, e.g., Salazar, M., et al., 1994, J.Mol.Biol. 241:440–55 and Egli, M., et al., 1993, Biochemistry 32:3221–37 (two stranded chimeric hybrid duplex of the form $r_3d_7 \cdot d_{10}$); Ban, C., et al., 1994, J.Mol.Biol. 236:275–85 (self complementary chimeric hybrid duplex of the form $d_5rphd_1D_4$); Chou, S. H., 1991, Biochemistry 30:5248–57 (self-complementing and non-self-complementing chimeric hybrid duplexes of the form $d_4r_4d_4$). The complementary strands of these duplex nucleic acids were not covalently bound to each other; they were associated only by Watson-Crick pairing.

A second group of scientists who have synthesized chimeric nucleic acids are those interested in the study and use of ribozymes, i.e., RNA molecules that are either self-cleaving or cleave other RNAs. Perreault, J. P., et al., 1990, Nature 344:565; Taylor, N. R., et al., 1992, Nucleic Acids Research 20:4559–65; Shimaya, T., 1993, Nucleic Acids Research 21:2605. These researches have found that chimeric ribozymes are active and are more resistant to nuclease digestion than RNA ribozymes. Chimeric ribozymes are self-complementary, i.e., the Watson-Crick paired strands are covalently linked. The compounds synthesized during the studies of chimeric ribozymes differ from the above-noted hybrid-duplex molecules, that were synthesized used for structural studies, in that chimeric ribozymes do not contain stable hybrid-duplexes. Thus, a chimeric ribozyme having DNA binding arms binds to its substrate and forms a hybrid duplex. Yang, J. H., et al., 1990, Biochemistry 29:11156–60. See also, Sawata, S., et al., 1993, Nucleic Acids Research 21:5656–60; Hendry, P., et al., 1992, Nucleic Acids Research 20:5737–41 Shimayama, T., 1993, Nucleic Acids Research 21:2605. The ribozyme catalyzes the cleavage of the RNA substrate and the hybrid-duplex is thus dissolved.

SITE-DIRECTED GENETIC ALTERATION IN EUKARYOTIC CELLS

Those skilled in the art of molecular biology recognize that on frequent occasions it is desired not merely to introduce a new polynucleic acid sequence, i.e, a new gene, into a targeted eukaryotic cell, but rather to alter a defined, pre-existing gene in the targeted cell. The targeted cell can be used in culture or it can be used to construct a transgenic animal.

A wide variety of techniques have been developed to introduce DNA into cultured eukaryotic cells. These techniques include calcium phosphate precipitation and DEAE-dextran mediated endocytosis, electroporation, liposome mediated fusion and transduction with replication incompetent viruses. However, while such techniques can quite often introduce functional genes into the eukaryotic cell, these techniques do not readily accomplish an alteration (mutation) in a specific existing gene. After introduction the exogenous DNA is isolated at a random position in the cell's genome by illegitimate recombination, rather than at a specific position by homologous recombination.

To date there is no generally satisfactory scheme for introducing a site-directed or site-specific genetic alteration (mutagenesis) in a higher eukaryote, i.e. in mammalian or avian cells. Although homologous recombination can be obtained in higher eukaryotic cells by introduction of very long (>1 kb) nucleic acids, these techniques require the application of elaborate selection techniques because the rate of illegitimate recombination in higher eukaryotes greatly exceeds that of homologous recombination. Thomas, K. R. & Capecchi, M. R., 1987, Cell 52:503. See, also, Valancius, V. & Smithies O., 1991, Mol. Cell. Biol. 11:4389 (comparison homologous recombination of linearized and supercoiled plasmids in eukaryotic cells).

One approach to achieving a predominantly site-directed mutagenesis has been the introduction of single stranded oligodeoxynucleotides directly into the cell. This techniques has been successfully employed in the yeast *Saccharomyces cerevisiae*, in which homologous recombination is significantly more active than it is in higher eukaryotes. Moerschell, R. P., et al., 1988, Proc.Natl.Acad.Sci. 85:524–28; Yamamoto, T., et al., 1992, Yeast 8:935–48. However, to date there have been no reports of the successful transformation of mammalian or avian cells by single stranded oligonucleotides.

A relationship between the structure of the target DNA and the rate of homologous recombination in mammalian can be inferred by studies that show that regions of alternating purine and pyrimidine bases, i.e., [d(TG)$_{30}$·d(AC)$_{30}$], display an entranced rate of recombination. These effects were demonstrated in studies of non-replicating plasmids in cultured mammalian cells. Wahls, W. P., et al., 1990, Mol. Cell. Biol. 10:785–93. These experiments were not extended to show recombination between an exogenous nucleic acid and the genome of the cell.

Attempts have been made to use RecA, a protein that promotes homologous recombination in the bacteria, *E. coli*, to promote homologous recombination in eukaryotic cells. However, these attempts have not been clearly successful. For example U.S. Pat. No. 4,950,599 to W. Bertling discloses a very low rate of site-directed mutation and no enhancement in the rate of homologous recombination by use of RecA in eukaryotic cells. Patent publications WO 93/22443 to D. Zarling and E. Sena, and publication 94/04032 to D. C. Gruenert and K. Kunzelmann both purport to correct a genetic defect in a cultured cell line related to cystic fibrosis. These publications disclose primarily experimental data that demonstrate the principle rather than data concerning examples of operative methods. Thus, to introduce polynucleotide/RecA complexes access to the nucleus, Zarling and Gruenert employ cells that were membrane-permeabilized, although such cells are incapable of further growth. Moreover, even when RecA-promoted homologous recombination was asserted to have taken place in intact cells, these publications provide no quantitative estimates of its frequency. Thus, the use of prokaryotic recA has not been convincingly shown to result in a rate homologous recombination in any viable eukaryotic cell significantly greater than the spontaneous rate of homologous recombination.

SUMMARY OF THE INVENTION

The present invention concerns single covalently linked duplex oligonucleotides that are homologous with a gene of interest having both deoxyribonucleotides and ribonucleotides. In order to effect a genetic change there are within the region of homology one or more non-corresponding (hereinafter "heterologous" or "mutator") base pairs. The normal, constitutive cellular processes of homologous recombination cause the mutator nucleotides to be inserted into the targeted genomic site. The duplex oligonucleotides of the invention (hereinafter "chimeric vectors") can be used to alter specifically a gene of interest by introducing into the gene the heterologous base pairs. The heterologous base pairs can be base pairs different from the gene of interest, or base pairs in addition to those present in the gene of interest (an insertion), or, lastly, the heterologous base pairs can be the absence of base-pairs found in the gene of interest (a deletion). The present invention is based, in part, on the discovery that the inclusion of a region of between about 15 and 50 base pairs of hybrid-duplex nucleic acid in the vector causes a greatly increased rate of alteration of the gene of interest. When the region of the heterologous base pairs is between 1 and 50 base pairs, the heterologous base pairs can be present in the vectors of the invention as either a homo-or a hybrid-duplex. When the heterologous base pairs are greater than 50 base pairs in length it is preferred that they be present as a homo-duplex.

The vector can be introduced into the target cell by any method known to allow for the introduction of nucleic acids into eukaryotic cells. Without limitation as to theory, the chimeric vector is believed to be engaged by the recombination/repair mechanisms of the target cell and to direct a the alteration of the target gene by gene conversion or by homologous recombination.

BRIEF DESCRIPTION OF THE FIGURES

FIGS. 1A and 1B shows the schematic representation of two chimeric vectors. The following are particularly labeled: 1, a first strand; 2, a second strand; 3, a heterologous region; 4, a homologous region; 5, a linker; 6, a ligation site.

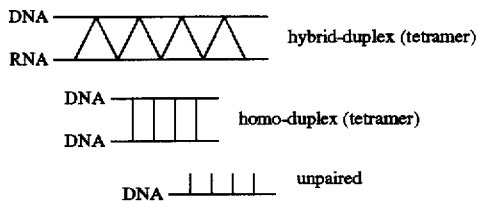

FIG. 1A is a ligated chimeric vector in the R-D-R form.

FIG. 1B is a hairpin chimeric vector in the R-D-R form having a single 3' and 5' end.

DETAILED DESCRIPTION OF THE INVENTION

DESCRIPTION OF THE CHIMERIC VECTORS OF THE INVENTION

The present invention encompasses duplex nucleic acids that contain both deoxyribose and ribose containing bases. Thus they contain regions of both DNA and RNA and are termed therefore termed "chimeric vectors." The 2'-O of the ribonucleotides of the chimeric vector can be methylated. Any phosphodiester can be substituted by a phosphorothiodiester or methyphosphonodiester.

The chimeric vectors of the invention are a single nucleic acid polymer. Accordingly; the chimeric vectors of the invention must contain at least one region of between at least 1 base and more usually 3 or 4 bases that are not Watson-Crick paired. These unpaired regions serve as linkers between the two strands of Watson-Crick paired bases. In contrast to other chimeric nucleotides that have been synthesized having regions of unpaired nucleotides chimeric vectors have no enzymatic activity i.e., they do not catalyze chemical reactions or themselves undergo chemical reaction in the absence of an biological energy source such as ATP.

The bases of the linkers in the preferred embodiment are deoxyribonucleotides. A chimeric vector having two linkers can be constructed so that the 3' and 5' ends of the polymer are Watson-Crick paired to adjacent nucleotides of the complementary strand. They can then be readily ligated so that the chimeric vector forms a single continuous circular nucleic acid polymer.

Substantially all the remaining bases of the chimeric vector are Watson-Crick paired. As used herein the statement that bases are Watson-Crick paired or that they form a duplex nucleic acid is to be understood to mean that under the proper conditions of temperature and salt they are capable of forming base pairs or a duplex nucleic acid. It is to be understood that under some conditions of low salt and/or elevated temperature the Watson-Crick base pairs may cease to be thermodynamically stable such that the duplex nucleic acid melts-out or denatures. It is also to be understood that a one or two base pair mismatch does not effect the operability of the invention.

The chimeric vectors of the present invention are intended for the purpose of specifically introducing alterations (a mutation) into a target gene. The genetic site of the alteration is determined by selecting a portion of the chimeric vector to have the same sequence as (to be homologous with) the sequence of the target site, hereinafter termed a homologous region. The area of differences between the sequence of the chimeric vector and the target gene are termed the heterologous region. Note that the chimeric vector is heterologous to the target gene, but is not a hybrid-duplex in this region of the vector. According to the preferred embodiment of the invention there are two homologous regions in each chimeric vector flanking the interposed heterologous region, all three regions being present in a single continuous duplex nucleic acid. Further according to the invention each homologous region contains a portion of hybrid-duplex nucleic acid. The portion of each hybrid-duplex can be at least 4 base pairs and preferably is 8 base pairs and more preferably about 20 to 30 base pairs. The function of the chimeric vector is not affected by a dinucleotide base pair of homo-duplex within a region of hybrid duplex, placed to allow ligation of the 3' and 5' ends to each other. The total length of the two homologous regions can be at least 20 base pairs and preferably is between 40 and 60 base pairs.

According to the invention, a region of homo-duplex nucleic acid can be disposed between the hybrid-duplex/homologous regions of the vector. The interposed homo-duplex can contain the heterologous region. When the heterologous region is less than about 50 base pairs and preferably less than about 20 base pairs, the presence of a interposed homo-duplex region is optional. When the heterologous region exceeds about 20 base pairs, an interposed homo-duplex that contains the heterologous region is preferred.

CONSTRUCTION OF THE CHIMERIC VECTORS OF THE INVENTION

The chimeric vectors of the invention can be synthesized by any method. The chimeric vectors can most readily be synthesized by modification of the techniques used in the solid phase synthesis of DNA. Reviewed Caruthers, M. H., 1985, Science 230:281–85; Itakura, K., et al., 1984, Ann.Rev.Biochem. 53:523–56. Modifications to permit the synthesis of RNA and of chimeric nucleic acids are disclosed in Scaringe, S. A., et al., 1990, Nucleic Acids Research 18:5433–41; Usman, N., et al., 1992, Nucleic Acids Research 20:6695–99; and Swiderski, P. M., et al., 1994, Anal. Biochem 216:83–88, which are hereby incorporated by reference in their entirety. Recent advances concerning the synthesis of chimeric nucleic acids are reviewed in Usman, N. & Cedergren, R., 1992, Trends Bioch. Sci. 17:334–9.

Chimeric vectors having a homo-duplex region interposed between two hybrid-duplex regions can be constructed using semisynthetic techniques. Two synthetic chimeric polynucleic acids having a hairpin conformation are to be constructed. The free 5' and 3' ends of the two chimeric nucleic acids are constructed with an overlap staggered ends complementary to the overlap of two different restriction enzyme digest products. A homo-duplex region is provided having the complementary restriction enzyme digested ends. The addition of a restriction enzyme sites to the ends of a cloned DNA fragment can be accomplished by techniques well understood by those skilled in the art, e.g., without limitation, PCR amplification with extended primers or the blunt end ligation of linkers containing the restriction site. The two chimeric nucleotides and the homo-duplex region can be ligated by conventional enzymatic techniques. The product, having chimeric oligonucleotides ligated at both ends can be separated from the incompletely reacted substrates by electrophoresis in 6% polyacrylamide gel in Tris Borate EDTA buffer under non-denaturing conditions. The linear capped molecules are constrained and are electrophoresed more slowly under these conditions.

Chimeric vectors containing only naturally occurring nucleotides can be used for the present invention. The chimeric vectors having regions of hybrid-duplex of about 20 ribonucleotides are found, in vitro, to be resistant to RNAse H. Resistance to enzymatic degradation can be obtained by the replacement of the ribonucleotides with 2'-O methylated ribonucleotides. Additionally or alternatively the phosphodiester bonds of the nucleic acid can be replaced by phosphorothiodiesters. Shimayama, T. et al., 1993, Nucleic Acids Research 21:2605. Arabinose containing nucleotides can also be used. As used herein the term nucleic acid is intended to encompass nucleic acids having these modifications.

THE USE OF THE CHIMERIC VECTORS OF THE INVENTION

The chimeric vectors of the present invention can be used to introduce a mutation in a specific location in the genome of a target cell. The specific location of the target location is defined by its nucleic sequence hereinafter the target sequence. According to the invention a chimeric vector is constructed wherein the homology regions are identical to the target sequence, except for the presence of some regions of hybrid-duplex. The change to be introduced is encoded by the heterologous region. The change may be change in one or more bases of the sequence or the addition of one or more bases. When the change in the target sequence is the addition of less than about 20 bases the invention may be practiced using one or two regions of hybrid duplex. When the change in the target sequence is the addition of more than about 50 bases it is preferred that the heterologous region be contained within a homo-duplex region.

The practice of the invention requires that the chimeric vector be introduced into the nucleus of the target cell. Any method which causes such introduction can be used. Such methods include electroporation, DEAE-dextran, Ca $PO_4$ precipitation, liposome mediated fusion (LIPOFECTIN), and direct injection. Electroporation is particularly suitable.

In one embodiment of the invention the chimeric vector can be used to construct transgenic animals. The chimeric vector can be introduced into the pronucleus of a ovum by direct injection, according to the method described Brinster, R. L. et al., 1989, PROC.NATL.ACAD.SCI 86:7087; see also U.S. Pat. No. 4,873,191 to T. E. Wagner and P. C. Hoppe, which are hereby incorporated by reference in their entirety. Alternatively, the chimeric vector can be introduced into an embryonic stem cell, chimeric animals can be produced by aggregation of the embryonic stem cell with normal blastocyst cells, and transgenic animals can be recovered as offspring of the chimeric animals, according to the method of Capecchi, M. R., 1989, Science 244:1288, which is hereby incorporated by reference in its entirety.

Using electroporation, as many as 1 cell per 10,000 treated cells can be specifically mutated at the target sequence (hereinafter "transformed"). The practice of the invention, thus, includes the use of a method to select the transformed cells from among the larger number of unmutated cells. In one embodiment the transformation of the cells confers a growth advantage. Non-limiting examples of such growth advantages include drug-resistance, alterations in growth regulation, and alterations in the capacity to utilize metabolites. In an alternative embodiment the method of selection can be negative selection whereby the transformed cells are rendered incapable of growth under the selecting conditions and the non-transformed cells are removed by exposure to conditions which selectively destroy proliferating cells.

Alternatively, the transformed cells may have an altered cell-surface antigenic phenotype that can be detected by immunofluorescence and selection can be performed by a Fluorescence Activated Cell Sorter.

When the method of introducing the chimeric vector into the cell is direct injection, as for example when constructing transgenic animals by pronuclear injection, the rate of transformation can be greater than 1 per 10,000 cells. The need for selection is thereby considerably reduced.

Typically useful amounts of a chimeric vector are between 10 and 1000 ng of chimeric vector per million cultured cells to be transformed by electroporation.

EXAMPLES

Example 1: In Vivo Activity in Ustilago Fungus

Wild-type Ustilago has a functioning ura-3 gene whose product is part of the uracil biosynthetic pathway. When wild-type Ustilago is grown on 5'-fluororotic acid (5FOA) -media the cells die due to incorporation of the acid into the pathway. If the ura-3 gene is mutated so that ura-3 mRNA is not produced, the cells survive on the 5FOA media.

The sequence of the endogenous ura-3 gene is known in the art. In one set of experiments, base 358 of the sequence was changed from a thymidine to an adenine which mutation results in a dysfunctional protein.

A chimeric vector was synthesized as follows: Vector for mutation at base 358: (358 RNA Vector)
5' TGCCGATCGGCAACTTTTGUUGCCGAUCGGCAA ATTT 3' (SEQ ID: 1)

The 358 vector adopts hairpin conformations. Underlined bases indicate ribonucleic acid residues. The bolded letter indicates the mutator (heterologous region). The italicized "T"'s indicate the unpaired bases.

A vector having the same sequence but containing no ribonucleic acids was also constructed for use as a control. In the vector thymidine was substituted for uracil.

The control vector for mutation at base 358: (DNA 358 Vector) 5' TGCCGATCGGCAACTTTTGTTGC-CGATCGGCAAATTT 3' (SEQ ID: 2) also adopts a hairpin conformation. Again, the bolded residue is the mutator.

An in vivo transformation experiment was carried out in which U. maydis cells ($10^7$) were made into protoplasts with a recovery of $10^6$ cells in a 50 µl transformation buffer solution following methods well known in the art and transfected with different amounts of the chimeric vectors or homogeneous (DNA alone) vector were mixed with the protoplasts at 37° C. The cells were then plated on selective media and the number of surviving colonies (transformants) were counted. The results are presented in tabular form below:

| Transfection Amount (µg) | Vector - 358 Type | Number of Surviving Colonies |
| --- | --- | --- |
| 0.1 | DNA | 0 |
| 0.1 | chimeric | 13 |
| 0.25 | DNA | 1 |
| 0.25 | chimeric | 49 |
| 0.75 | DNA | 12 |
| 0.75 | chimeric | 131 |
| 1.0 | DNA | 19 |
| 1.0 | chimeric | 573 |

These data show that transfection of cells with the RNA 358 Vector increases the survival of the cells at a much greater rate than transfection with the corresponding DNA vector.

Example 2: The Transformation of NIH 3T3 Cells.

NIH 3T3 cells are human cells that have a benign (controlled) growth characteristics. Malignant (uncontrolled) growth characteristics are conferred by the single point mutation in the oncogene H-ras that replaces $Gly^{12}$ by Thr. Thus, the mutation $G \rightarrow T^{12}$ leads to a readily selectable alteration in the growth characteristics. Taparowsky, E., et al., 1982, Nature 300:762; Sukumar S., et al., 1983, Nature 306:658.

Chimeric vectors were constructed to direct the $G \rightarrow T^{12}$ mutation having the following sequence:
5'-CACACCGACGGCGCCCACCACTTTGTGGTGGGC GCCGTCGGTGTGGGTTTGCC-3' (SEQ ID: 3)

The sequence is presented in the conventional single letter code with the additional features the RNA (underlined), unpaired bases are italicized, and the mutator base is bold. Note that after circularization the chimeric vector is divided into two substantially complementary strands by the two trithymidinyl sequences and that all the ribose containing nucleotides are present in only one of the two strands.

Two forms of the chimeric vector were synthesized using respectively one ("R") and two ("R-D-R") regions of hybrid duplex flanking four deoxyribose residues. The R-D-R form is shown above, SEQ ID: 3, the R form is identical except that bases 6–9 ("CGAC") were deoxynucleotides. Note that the 5' and 3' termini are deoxynucleotides. The allows the chimeric vectors to be circularized after synthesis by use of the same DNA ligase procedures as are commonly employed in recombinant DNA. After ligation, the circularization chimeric vectors were isolated from the substrate by two iterations of preparative electrophoresis in D600 gel (AT Biochem, Malvern, PA).

Control vectors were: 1) the same sequence lacking hybrid-duplex (data shown, "homo-duplex"); 2) the unpaired DNA (data shown "sDNA") having the sequence 5'- GCCCACACCGACGGCGCCACCAC-3' (SEQ ID 4); 3) the chimeric vector having no heterologous region and hence no mutator nucleotide (data not shown).

The experiment was conducted by transforming NIH 3T3 cells ($1 \times 10^6$ cells) using an electroporation procedure. After electroporation, the cells were plated at a seeding density of $4 \times 10^3$ cells/cm² and allowed to grow for 14 days in culture. Transformants were visualized by staining foci-forming cells with crystal violet. As a positive control, the plasmid pT24 that encodes the $T^{12}$ form of H ras was employed. This control was used to determine the level of illegitimate recombination in the transfected NIH 3T3 cells. The experiment was repeated five times and a summary of the results are presented in tabular form below. In addition to the results presented below the control experiments that used a chimeric vector having no mutator codon showed no transformed foci of NIH 3T3 cells.

| Vector Type | Amt Transfected (per 10⁶ cells) | Transformants per 10⁶ cells (14 days) | |
|---|---|---|---|
| pT24 (positive control) | 10 μg | 57 | |
| sDNA | 1 μg | 2 | |
| sDNA | 10 μg | 13 | |
| homo-duplex | 1 μg | 0 | |
| homo-duplex | 10 μg | 2 | |
| chimeric | 50 ng | R-D-R | R |
|  |  | 19 | 12 |
| chimeric | 200 ng | 55 | 43 |
| chimeric | 1 μg | 139 | 103 |

These results show that the chimeric vectors introduced a specific mutation by homologous recombination so as to transform mammalian cells. The rate of transformation in this experiment was greater than the rate of transformation by illegitimate recombination that was observed by transfection with pT24 positive control vector, which contained an entire mutated H-ras gene. Thus, by use of chimeric vectors a rate of homologous recombination in a mammalian cell was achieved that was greater than the rate of illegitimate recombination.

I claim:

1. A mixed ribo-deoxyribonucleic acid having at most one 3' end and one 5' end, which nucleic acid further comprises:
   a) at least one region of contiguous unpaired bases disposed so that the unpaired region separates the nucleic acid into a first strand and a second strand connected by said region of contiguous unpaired bases;
   b) at least one region of Watson-Crick paired nucleic acid of at least 15 base pairs in length, in which bases of the first strand correspond to bases of the second strand, and in which;
   c) the first strand comprises a region of at least three contiguous nucleotides comprised of a 2'-OMe ribose, which form a hybrid-duplex within the region of Watson-Crick paired nucleic acid.

2. The nucleic acid of claim 1, in which the second strand contains no nucleotides comprised of a 2'-OMe or 2'-O ribose and the first strand contains no nucleotides comprised of 2'-O ribose.

3. The nucleic acid of claim 1, which comprises between 15 and 50 base pairs of hybrid-duplex.

4. The nucleic acid of claim 1, in which the 5' and 3' ends are Watson-Crick paired to adjacent bases of a complementary strand in the region of Watson-Crick paired nucleic acid.

5. The nucleic acid of claim 4, which comprises between 15 and 50 base pairs of hybrid-duplex.

6. The nucleic acid of claim 5, in which the second strand comprises the 5' and 3' ends.

7. The nucleic acid of claim 6, in which the second strand contains no nucleotides comprised of a 2'-OMe or 2'-O ribose and the first strand contains no nucleotides comprised of 2'-O ribose.

8. The nucleic acid of claim 1, which further comprises a second region of contiguous unpaired bases disposed so that the unpaired region separates the nucleic acid into a first strand and a second strand connected by said second region of contiguous unpaired bases.

9. The nucleic acid of claim 8, in which the second strand contains no nucleotides comprised of a 2'-OMe or 2'-O ribose and the first strand contains no nucleotides comprised of 2'-O ribose.

10. The nucleic acid of claim 9, which comprises between 15 and 50 base pairs of hybrid-duplex.

11. The nucleic acid of claim 2, in which the first strand comprises two regions of nucleotides comprised of a 2'-OMe ribose that form two regions of hybrid-duplex, each hybrid-duplex region having at least 8 base pairs of length, and an interposed region of at least 4 base pairs of homo-duplex disposed between the hybrid duplex regions.

12. The nucleic acid of claim 11, in which the interposed region of homo-duplex consists of between 4 and 50 2'-deoxyribose base pairs.

13. The nucleic acid of claim 11, in which the interposed region of homo-duplex consists of between 30 and 1.000 2'-deoxyribose base pairs.

14. The nucleic acid of claim 13 in which the 5' and 3' ends are Watson-Crick paired to adjacent bases of a complementary strand in the region of Watson-Crick paired nucleic acid.

15. The nucleic acid of claim 9, in which the 5' and 3' ends are Watson-Crick paired to adjacent bases of a complementary strand in the region of Watson-Crick paired nucleic acid.

16. The nucleic acid of claim 15, which comprises between 15 and 50 base pairs of hybrid-duplex.

17. The nucleic acid of claim 16, in which the second strand comprises the 5' and 3' ends.

18. The nucleic acid of claim 2, in which the 5' and 3' ends are Watson-Crick paired to adjacent bases of a complementary strand in the region of Watson-Crick paired nucleic acid.

19. The nucleic acid of claim 18, which comprises between 15 and 50 base pairs of hybrid-duplex.

20. The nucleic acid of claim 19, in which the second strand comprises the 5' and 3' ends.

21. The nucleic acid of claim 12, in which the 5' and 3' ends are Watson-Crick paired to adjacent bases of a complementary strand in the region of Watson-Crick paired nucleic acid.

22. The nucleic acid of claim 21, which comprises between 15 and 50 base pairs of hybrid-duplex.

23. The nucleic acid of claim 22, in which the second strand comprises the 5' and 3' ends.

24. A method of introducing a predetermined alteration in a target sequence of the genome of a cultured cell, which cell contains a nucleus, which comprises the steps of:
   a) providing the mixed ribo-deoxyribonucleic acid of claim 1, which further comprises two regions homologous with a target sequence and a heterologous region, disposed there between, encoding the alteration; and
   b) maintaining said mixed ribo-deoxyribonucleic acid within the nucleus of the cultured cell,
whereby the alteration is introduced in the target sequence.

25. The method of claim 24, wherein the first strand of the mixed ribo-deoxyribonucleic acid, comprises two regions of contiguous nucleotides that form two regions of hybrid-duplex, each hybrid-duplex region having at least 4 base pairs of length, and an interposed region of at least 1 base pair of homo-duplex disposed between the hybrid duplex regions that comprises the heterologous region.

26. The method of claim 24, wherein the cell is other than a yeast or fungus.

27. The method of claim 26, which further comprises a step of introducing the mixed ribo-deoxyribonucleic acid into the nucleus by use of a liposome.

28. The method of claim 24, wherein the nucleus is a pronucleus of an ovum and the mixed ribo-deoxyribonucleic acid vector is introduced into the pronucleus by injection.

29. The method of claim 24, wherein the nucleus is a nucleus of an embryonic stem cell and the introduction is by use of a liposome or by electroporation.

30. A method of obtaining a cultured cell having altered characteristics which comprises the steps of:
   a) providing the mixed ribo-deoxyribonucleic acid of claim 1 which further comprises two regions homologous with a target sequence and a heterologous region, disposed there between, encoding the alteration;
   b) maintaining said mixed ribo-deoxyribonucleic acid within the nucleus of the cultured cell whereby the mixed nucleic acid and the target sequence recombine and the cell is altered; and
   c) selecting an altered cell.

31. The method of claim 30, wherein the first strand of the mixed ribo-deoxyribonucleic acid, comprises two regions of contiguous nucleotides that form two regions of hybrid-duplex, each hybrid-duplex region having at least 4 base pairs of length, and an interposed region of at least 1 base pair of homo-duplex disposed between the hybrid duplex regions that comprises the heterologous region.

32. The method of claim 30, wherein the cell is a mammalian cell.

33. The method of claim 30, wherein the cell is other than a yeast or fungus.

34. A method of introducing a predetermined alteration in a target gene of the genome of a cultured cell, which cell contains a nucleus, which comprises the steps of: a) providing a mixed ribo-deoxyribonucleic acid comprising
   i. a first and a second homologous region that are together from 20 to 60 nucleotides in length, which is homologous with the target gene; and
   ii. a heterologous region, that is disposed between the first and second homologous regions and is from 1 to 20 nucleotides in length, which is heterologous with the target gene and which contains the predetermined alteration,
   b) maintaining the mixed ribo-deoxyribonucleic acid vector within the nucleus of the cultured cell,
whereby the alteration is introduced in the target gene.

35. The method of claim 34, wherein the homologous regions comprise together between 20 and 60 2'-OMe ribonucleotides.

36. The method of claim 34, wherein the ribonucleotides of the mixed ribo-deoxyribonucleic acid are 2'-O-methylated.

37. The method of claim 34, wherein the heterologous region consists of deoxyribon nucleotides.

38. The method of claim 34, wherein the heterologous region is one nucleotide in length.

39. The method of claim 38, wherein the ribonucleotides of the mixed ribo-deoxyribonucleic acid are 2'-O-methylated.

40. The method of claim 34, wherein the alteration is an insertion or deletion in the target gene.

41. A mixed ribo-deoxyribonucleic acid for introducing a predetermined alteration into a target gene, which comprises:
   a) a first and a second homologous region that are together from 20 to 60 nucleotides in length, which is homologous with the target gene; and
   b) a heterologous region, that is disposed between the first and second homologous region and is from 1 to 20 nucleotides in length, which is heterologous with the target gene and which contains the predetermined alteration, wherein
the target gene is a gene of a cell having a nucleus.

42. The mixed ribo-deoxyribonucleic acid of claim 41, in which the first and second homologous regions together comprise between 20 and 60 2'-OMe ribonucleotides.

43. The mixed ribo-deoxyribonucleic acid of claim 41, in which the ribonucleotides of the mixed ribo-deoxyribonucleic acid are 2'-O-methylated.

44. The mixed ribo-deoxyribonucleic acid of claim 41, in which the heterologous region consists of deoxyribonucleotides.

45. The mixed ribo-deoxyribonucleic acid of claim 41, in which the heterologous region is one nucleotide in length.

46. The mixed ribo-deoxyribonucleic acid of claim 45, in which the ribonucleotides of the mixed ribo-deoxyribonucleic acid are 2'-O-methylated.

47. The mixed ribo-deoxyribonucleic acid of claim 41, in which the heterologous region contains an insertion or deletion of the target gene.

48. A mixed ribo-deoxyribonucleic acid having at most one 3' end and one 5' end, which nucleic acid further comprises:
   a) at least one region of contiguous unpaired bases disposed so that the unpaired region separates the nucleic acid into a first strand and a second strand connected by said region of contiguous unpaired bases;
   b) at least one region of Watson-Crick paired nucleic acid of at least 15 base pairs in length, in which bases of the first strand correspond to bases of the second strand; and, in which
   c) the first strand comprises a region of at least nine ribonucleotides, which form a hybrid-duplex within the region of Watson-Crick paired nucleic acid.

49. The nucleic acid of claim 48, in which the 5' and 3' ends are Watson-Crick paired to adjacent bases of a complementary strand of Watson-Crick paired nucleic acid.

50. The nucleic acid of claim 48, in which the second strand comprises the 5' and 3' ends.

51. The nucleic acid of claim 48, which comprises at least nine contiguous base pairs of hybrid-duplex.

52. The nucleic acid of claim 48, in which the first strand comprises two regions of contiguous nucleotides that form two regions of hybrid-duplex, each hybrid-duplex region having at least 4 base pairs of length, and an interposed region of at least 1 base pair of homo-duplex disposed between the hybrid duplex regions.

53. A method of introducing a predetermined alteration in a target sequence of the genome of a cultured cell, which cell contains a nucleus, which comprises the steps of:
   a) providing the mixed ribo-deoxyribonucleic acid of claim 48 which further comprises two regions homologous with a target sequence and a heterologous region, disposed there between, encoding the alteration; and
   b) maintaining said mixed ribo-deoxyribonucleic acid within the nucleus of the cultured cell,
whereby the alteration is introduced in the target sequence.

54. The method of claim 53, wherein the first strand of the mixed ribo-deoxyribonucleic acid, comprises two regions of contiguous nucleotides that form two regions of hybrid-duplex, each hybrid-duplex region having at least 4 base pairs of length, and an interposed region of at least 1 base pair of homo-duplex disposed between the hybrid duplex regions that comprises the heterologous region.

55. The method of claim 53, wherein the cell is other than a yeast or fungus.

56. The method of claim 55, which further comprises a step of introducing the mixed ribo-deoxyribonucleic acid into the nucleus by use of a liposome.

57. The method of claim 53, wherein the nucleus is a pronucleus of an ovum and the mixed ribo-deoxyribonucleic acid vector is introduced into the pronucleus by injection.

58. The method of claim 53, wherein the nucleus is a nucleus of an embryonic stem cell and the introduction is by use of a liposome or by electroporation.

59. A method of obtaining a cultured cell population having altered characteristics which comprises the steps of:
   a) providing the mixed ribo-deoxyribonucleic acid of claim 48 which further comprises two regions homologous with a target sequence and a heterologous region, disposed there between, encoding the alteration;
   b) maintaining said mixed ribo-deoxyribonucleic acid within the nucleus of the cultured cell whereby the mixed nucleic acid and the target sequence recombine and the cell is altered; and
   c) selecting an altered cell.

60. The method of claim 59, wherein the first strand of the mixed ribo-deoxyribonucleic acid, comprises two regions of contiguous nucleotides that form two regions of hybrid-duplex, each hybrid-duplex region having at least 4 base pairs of length, and an interposed region of at least 1 base pair of homo-duplex disposed between the hybrid duplex regions that comprises the heterologous region.

61. The method of claim 59, wherein the cell is a mammalian cell.

62. The method of claim 59, wherein the cell is other than a yeast or fungus.

* * * * *